US00PP08908P

United States Patent [19]

Walters, deceased

[11] Patent Number: Plant 8,908

[45] Date of Patent: Sep. 20, 1994

[54] VARIETY OF GERANIUM NAMED "BARONESS"

[75] Inventor: Ernest Walters, deceased, late of Hucknall, England, by Mary Bodill, administrator

[73] Assignee: Oglevee, Ltd., Connellsville, Pa.

[21] Appl. No.: 182,497

[22] Filed: Jan. 14, 1994

[51] Int. Cl.[5] ..... A01H 5/00
[52] U.S. Cl. ..... Plt./87.12
[58] Field of Search ..... Plt. 87.12

*Primary Examiner*—James R. Feyrer
*Attorney, Agent, or Firm*—Webb Ziesenheim Bruening Logsdon Orkin & Hanson

[57] ABSTRACT

'Baroness' has a wine red flower with a deep maroon blotch that appears almost black above a medium green foliage. It has smaller florets, but many more than the other Regal geranium currently on the market. Cutting production and rooting time are much better and lasting quality is improved also. Post harvest time is longer than the current varieties as well.

1 Drawing Sheet

BACKGROUND OF THE INVENTION

The present invention comprises a new and distinct cultivar of *Pelargonium*×*domesticum* known by the varietal name 'Baroness' (Oglevee No. 416; 'Walters Sunrise', No. 26). The new variety was discovered in a selected breeding program in Hucknall, Nottingham, Great Britain in the early to mid 1980's. The parentage of the new variety is not known with certainty but the breeding program of Ernest Walters, deceased, which extended more than 30 years, is described in a Walters article published in Volume 110, Part 8, August 1985, Journal of The Royal Horticultural Society. The new variety was first received in the United States in 1986 and was asexually reproduced by cuttings at Oglevee, Ltd. in Connellsville, Pa. in 1986. The new variety has been asexually reproduced by cuttings at Oglevee Ltd. in Connellsville, Pa. over a several year period. It has also been trial and field tested at Connellsville and has been found to retain its distinctive characteristics through successive propagations.

The cultivar when grown in a glass greenhouse in Connellsville, Pa. using natural light and 60° F. night, 68° F. day and 71° F. vent, has a response time of 14 weeks from a rooted cutting to flowering in a 6 inch pot. The response time was determined on plants grown in soilless media employing constant fertilizer 150–200 parts per million of nitrogen and potassium in full light. The rooted cuttings were potted on Nov. 2, 1992 and flowerd on Feb. 8, 1993.

DESCRIPTION OF THE DRAWINGS

The top photograph of the accompanying photographic drawing illustrates the inflorescence of the new cultivar, the color being as nearly true as possible with color illustrations of this type.

The bottom photograph of the accompanying photographic drawing illustrates the entire plant of the new cultivar, the color being as nearly true as possible with color illustrations of this type.

DESCRIPTION OF THE NEW PLANT

The following detailed description sets forth the characteristics of the new cultivar. The data which defines these characteristics were collected by asexual reproductions carried out by Oglevee Ltd. in Connellsville, Pa. The plant history was taken on six week plants blossomed under natural light in a greenhouse and the color readings were taken indoors under 200–220 foot candles of fluorescent cool white light. Color references are primarily to The RHS Color Chart of The Royal Horticultural Society of London.

THE PLANT

Classification:
- *Botanical.*—*Pelargonium*×*domesticum.*
- *Commercial.*—Regal geranium.

Form: Upright mound shaped habit.
- *Height.*—25–27 cm from media surface.
- *Growth.*—Controlled strong growth.

Strength: Continuous flowering; fast rooting.

Foliage: Stalked leaf attachment.

Leaves:
- *Size.*—8.5–10.0 cm across at the widest point.
- *Shape.*—Depressed ovate, truncate base.
- *Margin.*—Serrately lobed.
- *Texture.*—Leathery, slightly pubescent.
- *Color.*—Top: Green Group 137C. Bottom: Green Group 138B.
- *Ribs and veins.*—Palmate venation. Color: Yellow/Green Group 146B.

Petioles:
- *Color.*—Yellow/Green Group 146C.
- *Length.*—3.5–6.0 cm in length.

Stem:
- *Color.*—Yellow/Green Group 146C.
- *Internodes.*—1.0–3.0 cm in length.

THE BUD

Shape: Elliptical.

Size:
- *Umbel.*—2.0–2.5 cm across (no color showing).
- *Individual bud.*—0.5–1.0 cm across (no color showing).

INFLORESCENCE

Blooming habit: Many small florets opening slowly to form a full long-lasting flowerhead.
- *Size.*—8.5–10.0 cm across.
- *Borne.*—Florets on pedicel; pedicel on peduncle.

Florets:
- *Form.*—Cupped.

*Color.*—Top: Red/Purple Group 57B; Blotch on upper two petals Greyed/Purple Group 187A; Blotch on lower three petals Red/Purple Group 59B.

*Petals.*—5 petals; margin entire; separate not united.

*Size.*—5.5–6.5 cm across.

*Texture and appearance.*—Smooth and satiny; appearance from a distance is a wind red flower with a deep maroon blotch that appears almost black above medium green foliage.

Petaloids:

*Quantity.*—None present.

Pedicel:

*Length.*—2.5–3.0 cm.

*Color.*—Yellow/Green Group 146B.

Peduncle: 4.5–6.0 cm in length.

*Color.*—Yellow/Green Group 146B.

Disease resistance: None known.

Lasting quality: Continuous blooming; non-shattering.

REPRODUCTIVE ORGANS

Stamens:

*Anthers.*—3.0–4.0 mm in length.

*Filaments.*—1.0–1.5 cm in length. Color: White.

*Pollen.*—Golden Brown.

Pistils:

*Number.*—One; 5 to 7 parted.

*Length.*—1.5–2.0 cm in length.

*Stigma.*—5.-7 parted; Color: Red/Purple Group 60C.

*Style.*—1.0–1.2 cm in length; Color: Red/Purple Group 60C.

Ovaries:

*Color.*—Light Green, very pubescent; 5.0–6.0 mm in length.

Fruit: None observed.

GENERAL CHARACTERISTICS

'Baroness' has a wine red flower with a deep maroon blotch that appears almost black above a medium green foliage. It has smaller florets, but many more than the other Regal geraniums currently on the market. Cutting production and rooting time are much better and lasting quality is improved also. Post harvest time is longer than the current varieties as well.

It is claimed:

1. A new and distinct variety of geranium plant substantially as shown and described.

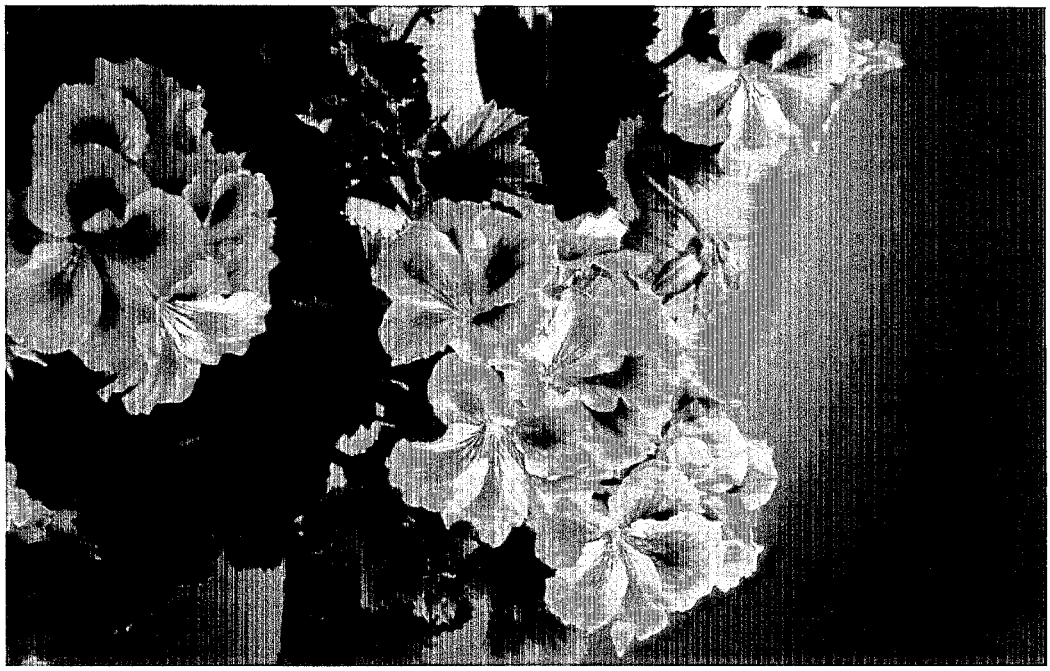
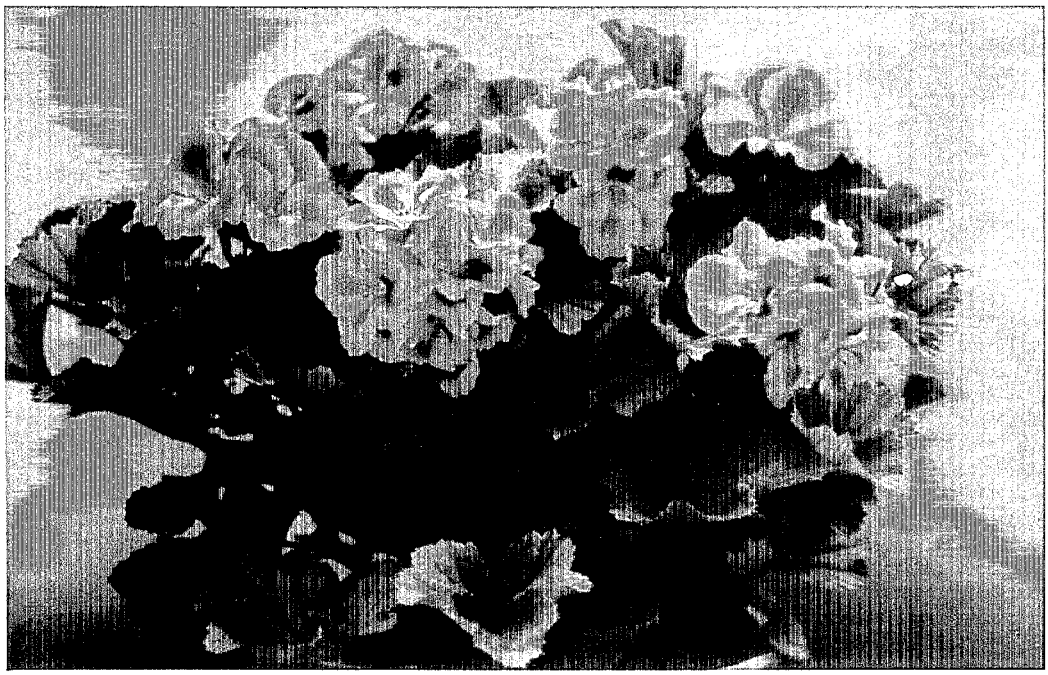

* * * * *